US00PP24025P2

(12) United States Plant Patent
Smith

(10) Patent No.: US PP24,025 P2
(45) Date of Patent: Nov. 12, 2013

(54) *CHRYSANTHEMUM* PLANT NAMED 'CIFZ0021'

(50) Latin Name: *Chrysanthemum×morifolium*
Varietal Denomination: CIFZ0021

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 132 days.

(21) Appl. No.: 13/385,260

(22) Filed: Feb. 10, 2012

(51) Int. Cl.
*A01H 5/00* (2006.01)

(52) U.S. Cl.
USPC ..... Plt./287

(58) Field of Classification Search
USPC ..... Plt./287, 291, 292
See application file for complete search history.

*Primary Examiner* — June Hwu
(74) *Attorney, Agent, or Firm* — Joshua L. Price

(57) ABSTRACT

A new *Chrysanthemum* plant named 'CIFZ0021' particularly distinguished by the small red-purple decorative inflorescences with medium green foliage, compact and mounded plant habit with a mid to late September natural flowering season.

1 Drawing Sheet

Latin name of the genus and species of the plant claimed: *Chrysanthemum×morifolium.*

Varietal denomination: 'CIFZ0021'.

BACKGROUND OF THE NEW PLANT

The present invention comprises a new *Chrysanthemum*, botanically known as *Chrysanthemum×morifolium*, and hereinafter referred to by the variety name 'CIFZ0021'.

'CIFZ0021' is a product of a planned breeding program. The new cultivar has small red-purple decorative inflorescences with medium green foliage, compact and mounded plant habit with a mid to late September natural flowering season.

'CIFZ0021' originates as a natural whole plant mutation of 'Yogigi Pink', U.S. Plant Pat. No. 19,666. 'CIFZ0021' was discovered and selected by the inventor as a single flowering plant within a large population of the parent cultivar grown massed in pots outdoors in a controlled breeding program in Alva, Fla. in November 2008. The parent cultivar 'Yogigi Pink' has pink and white two-toned colored inflorescences, the inflorescence color more fades with maturity, and has a slower natural season flowering response than that of 'CIFZ0021'.

The first act of asexual reproduction of 'CIFZ0021' was accomplished when vegetative cuttings were propagated from the initial selection in January 2009 in Alva, Fla.

BRIEF SUMMARY OF INVENTION

Horticultural examination of plants grown from cuttings of the plant initiated in 'CIFZ0021', and continuing thereafter, has demonstrated that the combination of characteristics as herein disclosed for 'CIFZ0021' are firmly fixed and are retained through successive generations of asexual reproduction.

'CIFZ0021' has not been observed under all possible environmental conditions. The phenotype may vary significantly with variations in environment such as temperature, light intensity, and day length.

Plant Breeder's Rights for this cultivar were applied for in Canada on Feb. 24, 2011, #11-7183; at the Community Plant Variety Office on Feb. 30, 2011, #2011-0794; and in the Republic of Korea on Jan. 31, 2012, #2012-79. 'CIFZ0021' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0021' with colors being as true as possible with an illustration of this type.

The photographic drawing shows a flowering potted plant of the new variety and a close-up of the inflorescences.

DETAILED BOTANICAL DESCRIPTION

The plant descriptions, measurements and aforementioned photographs were taken outdoors in Gilroy, Calif. in early August 2011. The plants were growing in an outdoor potted plant trial in one gallon pots in full sun. These plants were approximately 9-10 weeks of age.

Color references are made to The Royal Horticultural Society Colour Chart (R.H.S.) 2001.

TABLE 1

DIFFERENCES BETWEEN THE NEW VARIETY 'CIFZ0021' AND A MOST SIMILAR VARIETY

| | 'CIFZ0021' | 'PPP Belg 07' (U.S. Plant Pat. No. 20,430) |
|---|---|---|
| Bract quantity within the inflorescence head: | Less | More |
| Inflorescence color fading: | Fades less | Fades more |
| Plant overall size: | Smaller | Larger |

TABLE 1-continued

| DIFFERENCES BETWEEN THE NEW VARIETY 'CIFZ0021' AND A MOST SIMILAR VARIETY | | |
|---|---|---|
| | 'CIFZ0021' | 'PPP Belg 07' (U.S. Plant Pat. No. 20,430) |
| Black cloth flowering response: | Faster | Slower |

Plant:

*Form, growth and habit.*—Herbaceous garden-type. Stems upright and outwardly spreading, freely branching.

*Plant height.*—10.0-11.0 cm.

*Plant height (inflorescence included).*—13.0-15.0 cm.

*Plant width.*—30.0-33.0 cm.

Roots:

*Number of days to initiate roots.*—About 4 days at about 22 degrees C.

*Number of days to produce a rooted cutting.*—About 10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Between RHS 137A and RHS 137B.

*Lower surface.*—Closest to but lighter than RHS 137C.

*Mature, leaf color, upper surface.*—Between RHS 137A and RHS 137B.

*Lower surface.*—Closest to but lighter than RHS 137C.

*Length.*—2.2-2.4 cm.

*Width.*—2.0-2.2 cm.

*Shape.*—Ovate.

*Base shape.*—Attenuate.

*Apex shape.*—Mucronulate.

*Margin.*—Palmately lobed, irregularly incised and serrate.

*Texture, upper surface.*—Bifid T-shaped hairs.

*Lower surface.*—Bifid T-shaped hairs.

*Color of veins, upper surface.*—RHS 144B.

*Color of veins, lower surface.*—RHS 144B.

*Petiole color.*—RHS 144B.

*Length.*—0.7-1.2 cm.

*Diameter.*—0.2 cm.

*Texture.*—Bifid T-shaped hairs.

Stem:

*Quantity of main branches per plant.*—6-7.

*Color of stem.*—RHS 146A but a little lighter.

*Length of stem.*—6.0-8.0 cm.

*Diameter.*—0.3-0.4 cm.

*Length of internodes.*—0.5-0.9 cm.

*Texture.*—Bifid T-shaped hairs.

*Color of peduncle.*—Closest to but lighter than RHS 146A.

*Length of peduncle.*—4.5-5.5 cm.

*Peduncle diameter.*—0.2 cm.

*Texture.*—Bifid T-shaped hairs.

Inflorescence:

*Type.*—Compositae type, solitary, decorative-type, inflorescences borne terminally above foliage, ray florets arranged acropetally on a capitulum.

*Quantity of inflorescences per plant.*—About 60, and about 200 buds.

*Lastingness of individual blooms on the plant.*—About 6 weeks from first color.

*Fragrance.*—Slightly spicy.

Bud (just when opening/showing color):

*Color.*—Between RHS 187C and RHS 187D but a little more grey.

*Length.*—0.8-1.0 cm.

*Width.*—1.1-1.3 cm.

*Shape.*—Oblate.

Immature inflorescence:

*Diameter.*—2.9-3.2 cm.

*Color of ray florets, upper surface.*—Closest to RHS 70B with RHS 71A at the apex.

*Lower surface.*—RHS 70B with slight spot of RHS 71 A at the apex.

Mature inflorescence:

*Diameter.*—3.9-4.2 cm.

*Depth.*—1.5 cm.

*Total diameter of disc.*—Indistinct at this time.

*Receptacle height.*—0.3 cm.

*Receptacle diameter.*—0.5 cm.

Ray florets:

*Average quantity of florets.*—About 150-160 in numerous whorls.

*Color of florets, upper surface.*—Closest to RHS 72A with RHS 71A at the margins and apex.

*Lower surface.*—A light shade of RHS 70B with slight spot of RHS 71A at the apex.

*Length.*—1.5-1.8 cm.

*Width.*—0.6-0.65 cm.

*Shape.*—Oblong to slightly obovate.

*Apex shape.*—Irregularly emarginate to praemorse.

*Margin.*—Entire.

*Texture, upper surface.*—Papillose.

*Lower surface.*—Papillose.

Disc florets:

*Average quantity of florets.*—5-7.

*Color of florets.*—RHS 1C basally with RHS 15B apex.

*Length.*—0.25-0.3 cm.

*Width.*—0.1 cm.

*Shape.*—Tubular, elongated.

*Apex shape.*—Acute, 5 pointed.

Phyllaries:

*Quantity.*—20-25.

*Color, upper surface.*—RHS 138A but a little darker.

*Lower surface.*—RHS 138A.

*Length.*—0.35-0.5 cm.

*Width.*—0.1-0.15 cm.

*Shape.*—Lanceolate.

*Apex shape.*—Acute.

*Base.*—Fused.

*Margins.*—Entire, papery.

*Texture, upper surface.*—Bifid T-shaped hairs.

*Lower surface.*—Bifid T-shaped hairs.

Reproductive organs:

*Pistil.*—1, found on both types of florets.

*Length.*—0.45 cm.

*Style color.*—RHS 1C.

*Style length.*—0.35 cm.

*Stigma color.*—RHS 13B.

*Stigma shape.*—Bi-parted.

*Ovary color.*—RHS 155C.

*Ovary length.*—0.075 cm.

*Ovary width.*—0.1 cm.

*Stamens.*—4, found on only on the disc florets.

*Color of filaments.*—RHS 1C.

*Length filaments.*—0.2 cm.

*Anther color.*—RHS 15A.

*Anther length.*—0.1 cm.

*Anther shape.*—Oblong.

*Color of pollen.*—RHS 16A.

*Pollen amount.*—Normal/abundant.

What is claimed is:

1. A new and distinct variety of *Chrysanthemum* plant named 'CIFZ0021' substantially as illustrated and described herein.

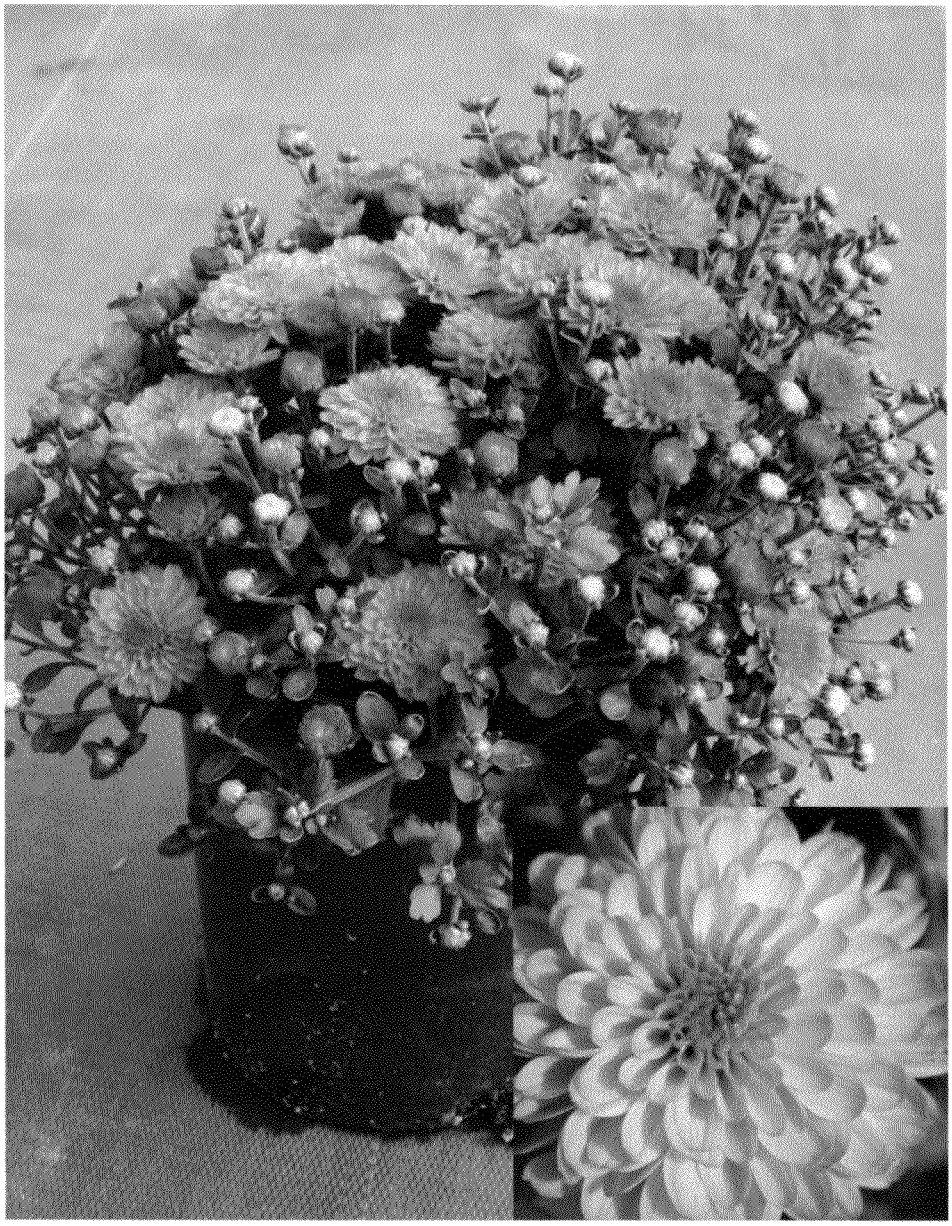

* * * * *